United States Patent [19]

Lia et al.

[11] Patent Number: 4,733,937
[45] Date of Patent: Mar. 29, 1988

[54] ILLUMINATING SYSTEM FOR ENDOSCOPE OR BORESCOPE

[75] Inventors: Raymond A. Lia, Auburn, N.Y.; Jane Anderegg, W. Vancouver, Canada

[73] Assignee: Welch Allyn, Inc., Skaneateles Falls, N.Y.

[21] Appl. No.: 920,159

[22] Filed: Oct. 17, 1986

[51] Int. Cl.[4] .............................................. G02B 23/26
[52] U.S. Cl. ............................... 350/96.26; 350/96.18; 350/432
[58] Field of Search ............... 350/96.18, 96.20, 96.24, 350/96.25, 96.26, 432; 128/6

[56] References Cited

U.S. PATENT DOCUMENTS

| | | | |
|---|---|---|---|
| 3,944,327 | 3/1976 | Larsen | 350/96.18 X |
| 4,266,534 | 5/1981 | Ogawa | 128/6 |
| 4,354,734 | 10/1982 | Nakahashi | 350/96.26 |
| 4,415,240 | 3/1983 | Nishioka et al. | 350/442 |
| 4,421,383 | 12/1983 | Carlsen | 350/96.20 X |
| 4,580,522 | 4/1986 | Nishioka et al. | 128/6 |
| 4,666,246 | 5/1987 | Nishioka et al. | 350/96.25 |

FOREIGN PATENT DOCUMENTS

| | | | |
|---|---|---|---|
| 0232525 | 11/1985 | Japan | 350/96.18 |
| 0004015 | 1/1986 | Japan | 350/96.26 |

Primary Examiner—Eugene R. LaRoche
Assistant Examiner—Seung Ham
Attorney, Agent, or Firm—Bruns and Wall

[57] ABSTRACT

An optical illuminating system for endoscope or borescope has a round fiber optic bundle light guide and a non-spherical lens disposed at the distal end of the light guide. The lens has a flat front surface and a compound rear optical surface formed of a central flat circular portion of smaller diameter than the fiber optic bundle light guide, and a frustoconic surface that flares back from the central surface beyond the diameter of the fiber optic light guide. The conic portion of this lens provides an annular distribution of light, and the disc portion provides a spot distribution to fill in the center of the annular distribution. The overall distribution is thus generally flat over an angle of up to 120 degrees.

10 Claims, 2 Drawing Figures

ILLUMINATING SYSTEM FOR ENDOSCOPE OR BORESCOPE

BACKGROUND OF THE INVENTION

This invention relates to endoscopes or borescopes and is more particularly directed to an illumination system comprising a fiber optic light guide that carries light to the distal end of the endoscope or borescope insertion tube and a distributing lens system capable of providing wide angle illumination of a target.

In a typical endoscope or borescope, a lens system, comprised of one or more conventional spherical lenses, is disposed in the head of the endoscope or borescope for spreading the light carried by the fiber optic light guide. A spherical lens has a generally bell-shaped light distribution. Hence, when the illumination angle becomes wider to correspond with a wide viewing angle, the difference in illumination between the center and the edges becomes greater. One reason for this edge illumination dropoff is the fourth-power-of-cosine law that applies to spherical lenses.

In addition to this infirmity, positive spherical lenses tend to focus light, and can cause a dot or mesh pattern of illumination to appear on the target, from the light emanating from the optical fibers, when an even blanket of light would be desired instead.

A number of previous attempts have been made to resolve the problem of wide angle distribution of light. In U.S. Pat. No. 4,415,240, a cylindrical reflecting member is placed between the distal end of the fiber optic light guide and the lens distribution system. However, the lenses of that system are positive spherical lenses. U.S. Pat. No. 4,580,522 describes a spherical lens illumination system in which a bar-shaped member is embedded at the center of the exit end of the fiber optic light guide, which reduces the light intensity at the center of the target. However, no attempt is made in either case to adjust the light distribution properties of the lenses themselves, so these previously proposed systems have not been able to provide the desired flat illumination distribution for extremely wide illumination angles.

OBJECTS AND SUMMARY OF THE INVENTION

Accordingly, it is an object of this invention to provide an illumination system for an endoscope or borescope which avoids the problems of spherical lens light distribution systems of the prior art.

It is a more particular object of this invention to provide a light distribution system which achieves wide angle illumination with even light distribution.

It is yet another object of this invention to provide an illumination system which employs a simple yet effective lens system, which has the advantages of low cost and ease of manufacture, and which can be made durable and resistant to abrasion.

In accordance with an aspect of this invention, the above objects are achieved with the optical illuminating lens of this invention which is employed in an endoscope or borescope in which a round fiber optic bundle carries light to the distal end of an endoscope or borescope for illumination of a target. This lens has a flat front surface and a compound rear optical surface. The rear surface is formed of a central circular flat surface, which is of smaller diameter than the diameter of the fiber optic bundle, and which define a central disc portion of the lens. Extending back from this central disc portion is a frustoconic or similar flared surface that surrounds the central circular surface portion. The flared surface extends back and outward from the circular surface portion beyond the diameter of the fiber optic bundle, and defines an outer portion of the lens. The rear surface fits against the fiber optic bundle with the lens central portion centered on the fiber optic bundle. This lens has the property that the outer portion distributes light from the bundle as a ring of light, while the central portion distributes the light as a spot to fill in the center of the ring. This creates a generally flat overall distribution.

In alternative embodiments, the front surface and the central portion of the back surface can be curved somewhat to effect a desired slight alteration of this distribution pattern, for example, to correct for parallax. Also, rather than being frustoconic, the flared portion may be somewhat toric.

This lens provides a substantially flat distribution of light over an angle of up to 120 degrees. Because of its simple and non-spherical shape, the lens can be of pressed glass rather than ground from a blank, thereby reducing manufacturing costs significantly.

The above and many other objects, features and advantages of this invention will be more fully understood from the ensuing detailed description of a preferred embodiment, which should be considered in connection with the accompanying drawing.

DETAILED DESCRIPTION OF THE PREFERRED EMBODIMENT

Figure 1:
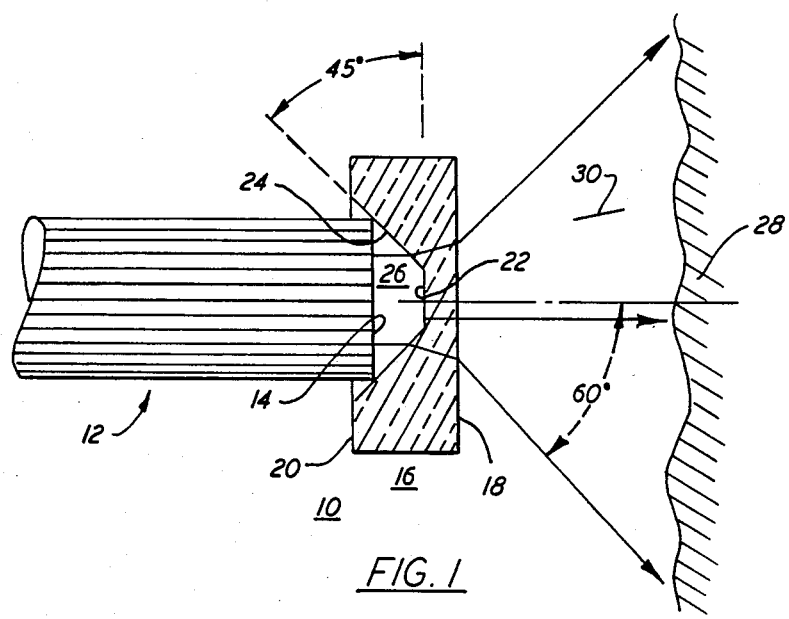
FIG. 1 is a schematic sectional view of a fiber optic bundle and distributing lens, which constitute the basic elements of the endoscope or borescope illuminating system according to an embodiment of this invention.

With reference to the drawing, FIG. 1 shows an optical illumination system 10 according to a preferred embodiment of this invention, here formed of a fiber optic bundle light guide 12 which has a polished flat front surface 14, and a pressed glass distribution lens 16 which has a flat front surface 18 and a compound rear surface 20. The rear surface 20 consists of a central flat disc portion 22, which here has a diameter about forty percent of the diameter of the fiber optic bundle front face 14, and a frustoconic surface 24 which extends from the edge of the disc portion 22 back beyond the edge of the front face 14 of the fiber optic bundle light guide 12. The frustoconic surface 24 defines an outer region of the lens 16. The fiber optic bundle light guide 12 fits snugly against the surface 24 and leaves an air-filled space 26 between the front surface 14 of the light guide 12 and the rear surface 20 of the lens 16. Although in this embodiment the space 26 is filled with air, it could instead contain another medium which has a refractive index less than that of the lens 16 or of the fiber optic light guide 12.

Figure 2:
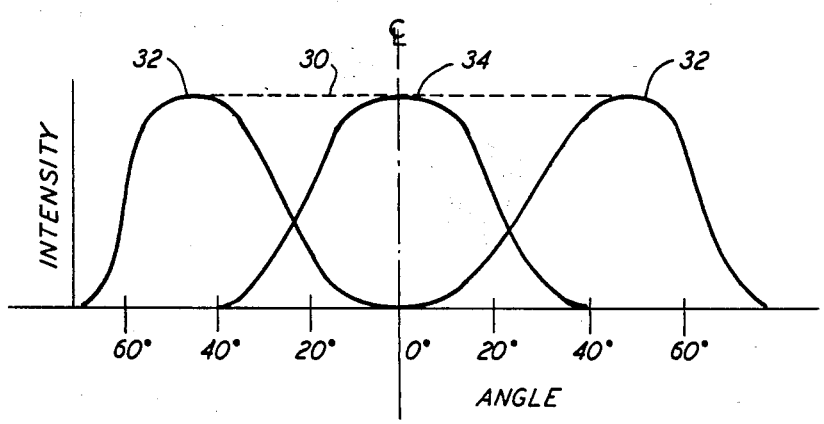
FIG. 2 is a chart of light intensity distribution of the embodiment of FIG. 1.

As shown schematically in FIG. 1, the optical illuminating system 10 provides a target 28 or other object to be illuminated with a generally flat distribution of illumination 30 over an angle of about sixty degrees or more from the center line or axis. This is achieved as follows:

The outer or frustoconic portion of the lens 16 has a generally ring-shaped distribution pattern 32, as illustrated in FIG. 2, i.e., a generally bell-shaped annular distribution. The flat portion defined by the disc 22 provided a spot distribution 34, which fills in the center of the annular ring. The intensities of these two distributions 32 and 34 add to achieve the overall flat distribution 30. As mentioned previously, the intention of this embodiment was to render the system as simple as possible. This achieves simplicity of manufacture and at the same time increases the flatness of light distribution over an extremely wide angle. However, by varying the shape of the lens slightly, the light distribution can be skewed somewhat to compensate for parallax.

This construction also has the advantage that the conic depression defined by the surface 24 on the rear of the lens 16 automatically centers the axis of the fiber optic bundle light guide 12 onto the axis of the lens 16.

With this construction, an illumination angle of one hundred twenty degrees of even light distribution can be achieved for optical wide angle viewing in endoscopes or borescopes. The spreading of illumination in this fashion is repeatable. The wide angle distribution is effected at low cost and with a great ease of manufacture. Also, the pressed-glass lens 16 is highly durable, and is easily treated for scratch resistance.

While the invention has been described with respect to a single preferred embodiment, it should be recognized that the invention is not limited to that embodiment and that many modifications and variations would present themselves to those of skill in the art without departing from the scope and spirit of this invention as defined in the appended claims.

What is claimed is:

1. An optical illuminating lens for use in an endoscope or borescope in which a round fiber optic bundle carries light through the endoscope or borescope to a distal end thereof, the lens having a front surface and a compound rear optical surface formed of a substantially flat central circular surface portion of smaller diameter than said fiber optic bundle defining a central portion of the lens and a flared surface surrounding said central circular surface portion and having a significantly sharper incidence angle, with respect to light from the fiber optic bundle, than said circular surface portion, the flared surface extending back from said circular surface portion out beyond the diameter of said bundle and defining an outer portion of the lens; the rear surface fitting against said bundle with the lens central portion centered thereof, such that the outer portion distributes the light from said bundle as a ring of light and said central portion distributes said light as a spot to fill in the center of said ring, thus creating an overall generally flat distribution.

2. An optical illuminating lens as recited in claim 1 wherein said flared surface portion is frustoconic.

3. An optical illuminating lens as recited in claim 1 wherein said front surface is substantially flat.

4. An optical illuminating lens as recited in claim 1 wherein a space is defined between said fiber optic bundle and the rear optical surface of said lens, and said space is filled with a medium of smaller refractive index than said fiber optic bundle or said lens.

5. An optical illuminating lens as recited in claim 1 in which the lens is formed of pressed glass.

6. An illuminating optical arrangement for an endoscope or borescope which comprises an optical fiber bundle light guide which consists of a multiplicity of optical fibers bound together in parallel in a generally cylindrical bundle and which terminates at a distal end thereof with polished ends disposed in a single plane; and a frustoconic distributing lens having a proximal surface facing the distal end of said optical fiber bundle light guide, said distributing lens including outer means aligned with an outer portion of the distal end of the light guide for distributing the light therefrom as a ring of light, and central means aligned with a central portion of the distal end of said light guide for distributing the light therefrom as a disc of light to fill the center of said ring of light, thus to create a substantially even distribution of illumination.

7. The illuminating optical arrangement of claim 6 in which said outer means includes a concave frustoconic lens portion and said central means includes a substantially flat lens portion.

8. The illuminating optical arrangement of claim 6 in which said frustoconic distributing lens is a single lens having a substantially flat distal surface and a compound proximal surface, said proximal surface including a central flat disc of lesser diameter than said fiber optic bundle light guide and with the front surface defining said central means, and a frustoconic surface flaring proximally outward from the edge of said central disc and with the front surface defining said outer means.

9. The illuminating optical arrangement of claim 6 in which said even distribution of light attains over a cone of illumination of at least substantially one hundred twenty degrees.

10. An optical illuminating lens for use in an endoscope or borescope in which a round fiber optic bundle carries light through the endoscope or borescope to a distal end thereof, the lens having a substantially flat front surface and a compound rear optical surface formed of a central circular surface portion of smaller diameter than said fiber optic bundle defining a central portion of the lens and a flared surface surrounding said central circular surface portion and having a significantly sharper incidence angle, with respect to light from the fiber optic bundle, than said circular surface portion, the flared surface extending back from said circular surface portion out beyond the diameter of said bundle and defining an outer portion of the lens; the rear surface fitting against said bundle with the lens central portion centered thereon, such that the outer portion distributes the light from said bundle as a ring of light and said central portion distributes said light as a spot to fill in the center of said ring, thus creating an overall generally flat distribution.

* * * * *